United States Patent
Lorusso et al.

(10) Patent No.: US 7,750,319 B2
(45) Date of Patent: Jul. 6, 2010

(54) METHOD AND SYSTEM FOR MEASURING CONTAMINATION OF A LITHOGRAPHICAL ELEMENT

(75) Inventors: Gian Francesco Lorusso, Overijse (BE); Rik Jonckheere, Muizen (BE); Anne-Marie Goethals, Oud-Heverlee (BE); Jan Hermans, Lummen (BE)

(73) Assignee: IMEC, Leuven (BE)

( * ) Notice: Subject to any disclaimer, the term of this patent is extended or adjusted under 35 U.S.C. 154(b) by 486 days.

(21) Appl. No.: 11/846,306

(22) Filed: Aug. 28, 2007

(65) Prior Publication Data

US 2008/0315125 A1 Dec. 25, 2008

Related U.S. Application Data

(60) Provisional application No. 60/840,899, filed on Aug. 28, 2006.

(30) Foreign Application Priority Data

Jan. 5, 2007  (EP) ................. 07000209

(51) Int. Cl.
G21K 5/04 (2006.01)
(52) U.S. Cl. .............. 250/492.2; 250/492.1; 250/504 R
(58) Field of Classification Search ............ 359/350, 359/353, 355; 250/492.1, 492.2, 492.22, 250/492.3, 504 R; 355/30, 67, 71, 77; 356/51, 356/433, 928, 954
See application file for complete search history.

(56) References Cited

U.S. PATENT DOCUMENTS

2003/0011763 A1  1/2003  Taniguchi et al.
2004/0218157 A1*  11/2004  Bakker et al. ............ 355/30
2005/0083515 A1  4/2005  Naulleau
2005/0162629 A1  7/2005  Moors et al.
2006/0001856 A1*  1/2006  Moors et al. ............ 355/69
2007/0139646 A1*  6/2007  Singh .................... 356/237.2
2007/0247600 A1*  10/2007  Kobayashi et al. ........ 355/30

FOREIGN PATENT DOCUMENTS

WO  WO 99/09399  2/1999

OTHER PUBLICATIONS

European Search Report dated Mar. 22, 2007 for EP Application No. 07000209.
Dean, et al. Effects of material design on extreme ultraviolet (EUV) resist outgassing, Advances in Resist Technology and Processing XXIII, Proc. of SPIE, Mar. 29, 2006, vol. 6153.

* cited by examiner

*Primary Examiner*—Jack I Berman
*Assistant Examiner*—Nicole Ippolito Rausch
(74) *Attorney, Agent, or Firm*—Knobbe Martens Olson & Bear LLP (57) ABSTRACT

A method and system for measuring contamination of a lithographic element is disclosed. In one aspect, the method comprises providing a first lithographical element in a process chamber. The method further comprises providing a second lithographical element in the process chamber. The method further comprises covering part of the first lithographical element providing a reference region. The method further comprises providing a contaminant in the process chamber. The method further comprises redirecting an exposure beam via the test region of the first lithographical element towards the second lithographical element whereby at least one of the lithographical elements gets contaminated by the contaminant. The method further comprises measuring the level of contamination of the at least one contaminated lithographical element in the process chamber.

24 Claims, 6 Drawing Sheets

METHOD AND SYSTEM FOR MEASURING CONTAMINATION OF A LITHOGRAPHICAL ELEMENT

CROSS REFERENCE TO RELATED APPLICATIONS

This application claims priority under 35 U.S.C. §119(e) to U.S. provisional patent application 60/840,899 filed on Aug. 28, 2006, which application is hereby incorporated by reference in its entirety.

BACKGROUND OF THE INVENTION

1. Field of the Invention

The present invention generally relates to lithography, more specifically lithography for semiconductor processing.

More specifically, this invention relates to a method for measuring contamination of a lithographical element. This invention also relates to a system for measuring contamination of a lithographical element.

2. Description of the Related Technology

Optical lithography nowadays uses wavelengths of 248 nm or 193 nm. With 193 nm immersion lithography integrated circuit (IC) manufacturing is possible down to 45 nm or even down to 32 nm node. However for printing in sub-32 nm half pitch node, this wavelength is probably not satisfactory due to theoretical limitations, unless double patterning is used. Instead of using wavelengths of 193 nm, a more advanced technology has been introduced, also referred to as extreme ultraviolet lithography (EUV lithography), which uses wavelengths of 10 nm to 14 nm, with a typical value of 13.5 nm. This technique was previously also known as soft X-ray lithography more specifically using wavelengths in the range of about 2 nm to 50 nm.

In optical lithography at some wavelengths in the deep ultra violet (DUV) range, the electromagnetic radiation is transmitted by most materials, including glass used for conventional lenses and masks.

At short wavelengths however, e.g. for extreme ultraviolet lithography and soft X-ray lithography, the electromagnetic radiation is absorbed by most materials, including glass used for conventional lenses and masks. Therefore a completely different tool is necessary for performing EUV lithography compared to conventional optical lithography. Instead of using lenses, such an imaging system presently relies on all-reflective optics and therefore is composed of reflective optical elements, also referred to as catoptric elements, for example mirrors. These reflective optical elements, e.g. mirrors preferably are coated with multilayer structures designed to have a high reflectivity (up to 70%) at the 13.5 nm wavelength. Furthermore, since air will also absorb EUV light, a vacuum environment is necessary.

Although EUV lithography is considered applicable using wavelengths less than 32 nm, still a lot of problems need to be overcome to reach a mature technology. As presented in a publication of K. R. Dean et al in Proc. of SPIE 6153E, p. 1-9 (2006), one of these problems is contamination of the optics by chemical components, also referred to as "contamination", which components are usually gaseous components originating from outgassing of the resist. This resist outgassing occurs due to the EUV irradiation of the EUV resist. It was noticed that at the regions where radiation falls on the EUV optics, the components contamination that outgases during the exposure may contaminate the EUV optics and as a consequence diminishes both the reflectivity of the reticle as well as the reflectivity of the imaging optics. As a consequence the lifetime of the EUV optics is reduced seriously due to contamination. Following the International Technology Roadmap for Semiconductors (ITRS) the organic material outgassing rate for 2 minutes under the lens should be lower than 5e13 molecules/$cm^2$-sec.

In order to reduce the resist outgassing rate, metrology tools are necessary which are able to measure the amount of resist outgassing for certain resists. One possibility for screening resist outgassing is also described in a publication of K. R. Dean et al in Proc. of SPIE 6153E, p. 1-9 (2006). An outgassing chamber is built on a synchrotron beam line. Together with the wafers, a $Si_3N_4$ witness plate is put in the chamber and exposed to EUV irradiation. This witness plate is then analyzed with electron spectroscopy for chemical analysis (ESCA) to find evidence of the contamination build up. The contaminants are collected in thermal desorption (TD) tubes. The contaminants in these TD tubes are analyzed by gas chromatography/mass spectroscopy (GC/MS) for chemical analysis.

US 2003/0011763 describes a projection exposure apparatus useful for projection exposure of a pattern defined on a mask onto a substrate in the manufacture of a semiconductor device. The apparatus comprises a cleaning device for cleaning an optical member. Contamination of a substrate-opposed surface of an optical member at the time of pattern transfer can be reduced by, prior to pattern transfer, removing the contaminants caused by the previous pattern transfer by a cleaning operation. In embodiments of US 2003/0011763, the cleaning operation may be performed only when a numerical value for a contamination level which is determined based on a difference between a predetermined reflectance and an actually determined reflectance of the optical member is out of a certain permissible range. The predetermined reflectance is determined immediately after the apparatus is manufactured.

US 2005/0083515 describes a method for evaluating reflection uniformity of an optical component having EUV reflective surface for use in EUV lithography. The method may be used to determine coating and substrate induced reflectivity losses of a substrate. According to embodiments of US 2005/0083515 a reflectivity map of a test piece is compared to a reference piece of identical design that has been independently characterized.

Other techniques and systems still are required to analyze resist outgassing, with a special interest for in-situ measurement of the contamination.

SUMMARY OF CERTAIN INVENTIVE ASPECTS

Certain inventive aspects provide good methods and systems for characterizing contamination of a lithographical element. It is an advantage of embodiments of the present invention to provide methods and systems for directly measuring a parameter of a contaminated lithographical element, such as a contaminated lithographical optical element, e.g. measuring reflectivity or transmissivity of the contaminated lithographical element which may be a reflective optical element, e.g. a mirror, or such as a contaminated reticle. According to some embodiments of the present invention, a method for measuring the contamination of a lithographical element compares a parameter of a contaminated lithographical element with a reference parameter relevant for this lithographical element in uncontaminated condition. Directly measuring thereby may be measuring a parameter on the lithographical element itself.

According to some embodiments of the present invention, the parameter, e.g. reflectivity, is measured in the process chamber, which means that ex-situ reflectance measurements are generally unnecessary. It is an advantage of such embodiments that parameters of the process chamber, such as e.g. the irradiation source used, can be directly taking into account. According to some embodiments of the present invention, the parameter, e.g. reflectivity, is measured in the process chamber of a metrology system. According to some embodiments of the present invention, the parameter, e.g. reflectivity, is measured in the process chamber of a lithographic process system. The method avoids to a large extent manipulation of the lithographical elements, hence reduces the risk on variation of the measured value due to manipulation of the contaminated lithographical elements. The method avoids the use of vulnerable reference optical elements such as reference mirrors. The method allows an in-situ measurement of relevant optical parameters of the contaminated element, and reduces the necessity of expensive and time consuming test setups and recalibration procedures.

It is an advantage of embodiments of the present invention to provide a system for performing the method according to certain embodiments. According to some embodiments of the present invention, the system may be a metrology system or a lithographic process system.

According to a first aspect of the present invention, a method is provided for measuring contamination of a lithographical element, the method comprising:

providing a first lithographical element in a process chamber, providing a second lithographical element in the process chamber, covering part of the first lithographical element, providing a reference region on the first lithographical element being the covered part of the first lithographical element and a test region on the first lithographical element being the uncovered part of the first lithographical element;

providing a contaminant in the process chamber, directing an exposure beam on the test region of the first lithographical element and the second lithographical element whereby at least one of the lithographical elements gets contaminated by the contaminant, measuring the level of contamination of the at least one contaminated lithographical element in the process chamber.

The method preferably comprises uncovering the covered part of the first lithographical element, providing an uncovered reference region. The measuring the level of contamination preferably comprises optically measuring the level of contamination.

It is an advantage of certain embodiments that optical measurements are used on the same object, as this allows to work with the same parameters/conditions of that object, therefore providing more accurate parameters and therefore more accurate determination of the contamination level. By using a test region and a reference region on the same object, a more precise correlation can be made.

It is an advantage of embodiments of the present invention that contamination can be measured in the process system. It is an advantage of embodiments of the present invention that contamination can be measured using the same light beam as exposure beam as well as optical measurement beam. It is an advantage of embodiments of the present invention that contamination is measured by determining optical properties of the contaminated component alone, it is that no separate element is required.

According to some embodiments of the present invention, the process of covering part of the first lithographical element may comprise the provision of a shield to cover part of the first lithographical element and providing a hard contact, i.e. direct contact, between the shield and at least part of the first lithographical element.

According to other embodiments of the present invention, the process of covering part of the first lithographical element may comprise the provision of a shield to cover part of the first lithographical element and providing a soft contact between the shield and at least part of the first lithographical element.

Optically measuring the contamination level may comprise measuring an optical parameter on a test region and a reference region.

According to some embodiments of the present invention, the process of covering part of the first lithographical element may comprise the provision of a shield for shadowing at least part of the first lithographical element.

According to some embodiments of the present invention, resist may be provided in the process chamber, and the contaminant may be provided in the process chamber by outgassing of the resist. The first lithographical element may be a lithographical optical element.

According to some embodiments of the present invention, the first lithographical element may be a mirror or a lens.

According to some embodiments of the present invention, the method further may comprise removing the contaminant from the process chamber before measuring the level of contamination of the at least one contaminated lithographical element in the process chamber. Removing the contaminant may comprise removing the contamination source. Removing the contaminant furthermore may comprise reducing the remaining contamination present in gaseous form in the chamber. Removing the contaminant may comprise removing a lithographic element comprising a resist layer on top and/or removing the outgassing gas outgassed by the resist layer from the process chamber. Removing the contaminant also may be removing contamination gasses previously introduced in the chamber. Such a removal may e.g. be performed by purging the chamber with a purge gas or by pumping down the chamber to a predetermined level.

Optically measuring the contamination level may comprise measuring an optical parameter on a test region and the uncovered reference region.

According to some embodiments of the present invention, the method further may comprise cleaning the process chamber before measuring the level of contamination of the at least one contaminated lithographical element in the process chamber.

According to some embodiments of the present invention, the at least one of the contaminated lithographical element is the first lithographic element.

According to some embodiments of the present invention, the process of measuring the level of contamination of the at least one lithographical element in the process chamber may comprise measuring the level of contamination of the first lithographical element.

According to some embodiments of the present invention, the process of measuring the level of contamination of the first lithographical element in the process chamber may comprise:

measuring a value for a parameter at the uncovered reference region of the first lithographical element, being the reference value of the parameter, measuring a value for the parameter at the test region of the first lithographical element, being the test value of the parameter, determining, e.g. by calculation, the difference between the reference value and the test value.

According to some embodiments of the present invention, the process of measuring the reference value of the parameter may comprise:

redirecting the exposure beam via the reference region of the first lithographical element towards a sensor. Alternatively, different beams could be used for exposing the lithographic elements and for optically measuring.

According to some embodiments of the present invention, the process of measuring the test value of the parameter may comprise:

redirecting an exposure beam via the test region of the first lithographical element towards a sensor.

According to some embodiments of the present invention, the second lithographical element may comprise the contaminant. According to some embodiments of the present invention, the second lithographical element may comprise resist, the resist comprising the contaminant.

According to some embodiments of the present invention, the second lithographical element may be a lithographical optical element. Possibly the second lithographical element is a mask.

According to some embodiments of the present invention, the providing of a contaminant in the process chamber may comprise providing gaseous compound in the chamber.

According to some embodiments of the present invention, at least the second lithographical element may be contaminated by the contaminant in the process of redirecting an exposure beam via the test region of the first lithographic element towards the second lithographical element. According to some embodiments of the present invention, the process of measuring the level of contamination of the at least one lithographic element in the process chamber may comprise measuring the level of contamination of the at least second lithographical element in the process chamber.

According to some embodiments of the present invention, the process of measuring the level of contamination of the at least second lithographical element may comprise:

measuring a second element test value for the parameter at the test region of the second lithographical element by redirecting the exposure beam via the reference region of the first lithographical element towards the second lithographical element and further towards a sensor.

According to some embodiments of the present invention, the process of measuring the second element test value further comprises: redirecting the exposure beam via the test region of the first lithographical element towards the second lithographical element towards a sensor.

According to some embodiments of the present invention, the first lithographic element may be a mirror. According to some embodiments of the present invention, the parameter measured may be the reflectivity of the first lithographic element. The sensor may be a reflectivity sensor.

According to some embodiments of the present invention, the first lithographic element may be a lens. According to some embodiments of the present invention, the parameter measured may be the transmissivity of the first lithographic element. The sensor may be a transmissivity sensor.

According to some embodiments of the present invention, the sensor may comprise a diode.

According to some embodiments of the present invention, the test region may comprise a plurality of test zones. The reference region may comprise a plurality of reference zones.

According to a second aspect of the present invention, a system for measuring contamination of a lithographic element is provided, which system comprises:

a process chamber,
an inlet for introducing a contaminant.

a first energy source for providing a first energy beam in the process chamber, the energy beam at least adapted to cause contamination of at least one of the lithographic elements by directly or indirectly exposing the at least one of the lithographic elements in the presence of the contaminant;

an element for covering at least part of the first lithographic element for providing a reference region on the first lithographic element, whereby the element for covering is adapted such that the reference region is not contaminated when the first lithographic element is exposed by the first energy beam, and a sensor for measuring contamination.

The system may comprise an element for introducing a first lithographic element into the process chamber and an element for introducing a second lithographic element into the process chamber. According to embodiments of the present invention, the first energy beam may be adapted for measuring a parameter of the at least one of the lithographic elements. According to embodiments of the present invention, the system further may comprise a second energy source for providing a second energy beam in the process chamber, the second energy beam is adapted for measuring a parameter of the at least one of the lithographic elements.

According to embodiments of the present invention, the process chamber may be a vacuum process chamber.

According to embodiments of the present invention, the first energy source may emit electromagnetic radiation in the extreme ultra-violet range.

According to embodiments of the present invention, the sensor may be a reflectivity sensor or a transmissivity sensor. The sensor may be an optical sensor. According to embodiments of the present invention, the sensor may comprise a diode.

Another inventive aspect also relates to a method for measuring in a process chamber contamination of a lithographical element from a lithographical system, the process chamber comprising at least a first lithographical element and a second lithographical element, the method comprising:

providing a contaminant in the process chamber exposing a test region of the first lithographical element and the second lithographical element whereby at least one of the lithographical elements gets contaminated by the contaminant, leaving part of the at least one of the lithographical elements unexposed resulting in a reference region of the at least one contaminated lithographical element, and optically measuring the level of contamination of the at least one contaminated lithographical element in the process chamber by measuring an optical parameter on the test region and the reference region of the at least one contaminated lithographical element.

Other features and characteristics of the method and corresponding system may be as set out in the other methods and systems described herein.

In another inventive aspect, a system for measuring contamination of a lithographical element is disclosed. The system comprises means for accommodating a first lithographical element, a second lithographical element, and a contaminant. The system further comprises means for covering part of the first lithographical element, thus providing a reference region on the first lithographical element being the covered part of the first lithographical element and a test region on the first lithographical element being the uncovered part of the first lithographical element. The system further comprises means for directing an exposure beam via the test region of the first lithographical element towards the second lithographical element such that at least one of the lithographical elements gets contaminated by the contaminant.

The system further comprises means for uncovering the covered part of the first lithographical element, thus providing an uncovered reference region. The system further comprises means for optically measuring the level of contamination of the at least one contaminated lithographical element in the process chamber.

Different advantages of the proposed embodiments with respect to prior art may be obtained. In the prior art contamination measurements of a lithographical element, more specifically lithographic optics are done by collecting various contaminating chemical components and by analyzing these chemical components with a mass spectrometer or a similar analysis technique such as mentioned in a publication of K. R. Dean et al in Proc. of SPIE 6153E, p. 1-9 (2006). The contaminants are collected in thermal desorption (TD) tubes. The contaminants in these TD tubes are analyzed by gas chromatography/mass spectroscopy (GC/MS) for chemical analysis. This technique of collecting the contaminating chemical components is not repeatable, as the samples are destructed. The results hence suffer from relatively large statistical variation.

The understanding of the impact of these contaminating components on the optical lithographical elements further requires complex calculations and simulations, thus introducing additional uncertainty and variation.

With various embodiments of the present invention this disadvantage of chemical analysis techniques is at least partially overcome by directly measuring a parameter of the contaminated lithographical optical element itself, e.g. measuring reflectivity or transmissivity of the contaminated mirror, or e.g. measuring reflectivity or transmissivity of the contaminated reticle. The parameter, e.g. reflectivity, is measured in the process chamber, which means that ex-situ reflectance measurements are generally unnecessary.

Generally a reflectance measurement, e.g. with a standard reflectometer, is conducted by monitoring source and sample simultaneously to obtain a value representing the reflection of the sample with regard to a reference. This approach requires a reference mirror to split the incident beam and may require the provision of an additional second detector. For measuring contamination of a lithographical element, the requirements are very stringent. A long term reflectivity change of about 1% is expected, which means that a repeatability of 0.1% or better is aimed for. The stability of the reference mirror, as used in general reflectance measurements, may be a serious problem, because it will become contaminated as well over time, although at a much slower rate, thus creating artifacts. Similarly, the fact that two detectors may be necessary, may create a problem. To avoid artifacts, complex recalibration procedures are needed, together with golden standards in terms of mirrors and detectors. With the embodiments of the present invention some or even all these problems and disadvantages of standard reflectometry measurements may be overcome. Only one detector may be used and the reference mirror is integrated on the sample, e.g. mirror or reticle, itself as the reference region.

Further, in standard reflectometry, the use of a reference mirror is further complicated by the fact that mirrors with different composition and stack need to be tested. This means that different samples will require different reference mirrors, as well as different recalibration procedures. These disadvantages can be overcome by the embodiments of the present invention where different reference regions and different test regions on one sample (e.g. mirror) may be provided.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

In the different figures, the same reference signs refer to the same or analogous elements.

DETAILED DESCRIPTION OF CERTAIN INVENTIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, over and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

The following terms are provided solely to aid in the understanding of the description.

The term "outgassing" is to be understood as the release of gaseous contamination by facilities, equipment, or tools or components thereof in a clean room and/or in process chambers; the term also may be referred to as offgassing.

With resist outgassing is meant that gases or vapors are released by the resist in a lithographic process over a period of time.

With "shielding" is meant that a region of a lithographic element is prevented of being irradiated with a radiation, such that it will not be contaminated when being subjected to a contaminant and irradiation. A number of ways for shielding may be provided.

Hard contact is to be understood as providing a contact between a shield or cover and a lithographic element substantially "no spacing" is in between the shield or cover and the lithographical element, i.e. the shield or cover and the lithographic element are in direct contact with each other. The contact may be air-tight, so that no gaseous contamination can reach the contacted area of the lithographic element, although the embodiments of the present invention are not limited thereto.

Soft contact is to be understood as providing shielding by a shield on a lithographic element. Such shielding preferably is such that substantially no irradiation can reach the shielded area of the lithographic element or that the irradiation that can reach the shielded area is substantially reduced compared to when direct irradiation would be possible. For this purpose, the shield may be provided in proximity to the lithographic element. The latter may e.g. be at a distance less than about 1 mm. Such a reduction may be, e.g., a reduction with about 60%, more preferably with 80%, even more preferably with 95%, still more preferably with 99%. The shielding thus may be shadowing whereby the shield is positioned separately from the lithographic element but such that incident radiation is not passed through the shield, which shield throws a shadow on a region of the lithographic element which is thus prevented on being directly irradiated.

The term "Extreme ultraviolet radiation" includes electromagnetic radiation in the wavelength range of about 31 nm to 1 nm.

The term "X-ray radiation" typically includes electromagnetic radiation in the wavelength range of about 10 nm to 0.01 nm.

The term "deep ultraviolet radiation" is typically electromagnetic radiation in the wavelength range of about 300 nm to 7 nm.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

The embodiments of the present invention are suitable for lithographic systems and methods using electromagnetic radiation with wavelengths having the same order of magnitude or being smaller than the reticle feature thickness. The latter typically includes extreme ultraviolet (EUV) radiation, deep ultraviolet and X-ray radiation. It is to be noticed that the invention is not limited thereto and that slight variations in wavelength range may occur.

The embodiments of the present invention typically may be related to a lithographic metrology system. A lithographic metrology system is used typically for characterization and/or optimization of parameters in a lithographic process or in a lithographic process system. A lithographic process is typically performed in a lithographic process system, also often referred to as lithographic exposure tool. The embodiments of the present invention may also be related to a lithographic process system.

The term "contaminant" as referred to in this application is used to define an object, a material or a substance which induces contamination. Contaminant may be for example—but not limited thereto—formed by or related to a solid or gaseous contaminant, e.g. originating from a photoresist. Contaminants also may be present in gaseous form in any other suitable way. Contamination may be introduced by the presence of foreign species, such as e.g. water vapor or hydrocarbons in the vacuum and/or e.g. either by resist outgassing, e.g. yet only hydrocarbons, or intentionally introduced components through the leak valve. Contamination also may refer to a reduction of reflectivity by adsorbed species, also referred to as reflectivity loss or absorbed contamination. When photoresist is exposed, resist outgassing occurs. Resist outgassing is caused by photo-products which outgas from the resist, when exposed. These outgassed components will condense on the exposure tool's optical elements degrading the optics of the lithographic system. Contamination of components may occur on the optical components and on other parts of the chamber, during exposure or at periods without exposure. Nevertheless, when exposure is performed, contamination on irradiated surfaces is significantly higher and in some embodiments of the present invention the main focus is on contamination of irradiated surfaces.

Typically for advanced photolithography chemically amplified photoresists are used. These resists contain photo-acid generators (PAGs) which outgas under EUV radiation under vacuum. In general a resist consists of a polymer backbone, a solvent, protection groups, quenchers and proprietary additives. The most common outgassing products are from the protective groups and decomposition products from the PAG. In EUV lithography, also contamination occurs due to the hydrocarbons from the outgassing components from the resist polymer itself during the EUV radiation in the vacuum environment. Possible resist outgassing components may be for example—but not limited thereto—isobutane, isobutene, acetone, tert-butyl-benzene, methylstyrene, hydronaphthalene, benzene and alike depending on the resist which is used. Another contaminant may also be any (inorganic or organic) compound which is added into the lithographic system, for example via a gas inlet, and which may induce contamination on the lithographic optics, e.g. from cleanroom air, e.g. filtered particles, usually not molecular contaminants; from cleanroom materials, e.g. floor covering, filters, sealing materials, tubing, wafer boxes, wafer carriers, adhesives and tapes used in mounting pellicles, as well as monomers and oligomers, e.g. caprolactam from Nylon vessels, silicones, siloxanes from sealing materials, additives like process enablers and stabilizers, plasticizers e.g. dioctyl phthalate, dibutul phthalate, cross-linking agents, diacetyl benzene, anti-oxidants like benzoquionones, fire retardants like organophosphates, tributylphosphate. A lithographic system (e.g. EUV tool, immersion tool, . . . ) is typically installed in a cleanroom environment and by introducing e.g. a wafer from this cleanroom environment into the lithographic system, the organic compounds present in this cleanroom environment may enter the lithographic system and form a source of contamination.

The term "lithographic optical element" as referred to in this application is used to define an optical element, which is typically used in a lithographic process system. Depending on the wavelengths of the electromagnetic radiation used in the lithographic process, different optical elements are used. For example, in an EUV lithographic system, the optical elements presently need to be reflective since a wavelength of 13.5 nm is used in vacuum. At least four optical components are required for EUV lithographic exposure: a collector which captures as much radiation from the illumination source as possible, an illumination system which homogeneously illuminates the used field on the mask, the mask itself containing the pattern to be transferred to the wafer substrate, and imaging optics which demagnify the structures from the mask to the wafer. For EUV lithography, all these optics presently consist of reflective elements such as mirrors. Also the mask, also often referred to as reticle, is an optical element, more specifically being a reflective mirror. A reticle is typically a kind of mask used for a stepper or scanner, typically using reduction optics, such that the image on the reticle is magnified. A mask/reticle is a plate with a pattern of transparent and opaque areas used to create patterns on wafers. For EUV lithography, the mask/reticle starts out as a perfect EUV mirror, and the pattern is applied on the top surface, either as an absorbing layer, or through etching into the mirror to make some parts non-reflective. An EUV mirror (e.g. used in the illumination system) starts out as a curved but atomically flat surface, to which a special multilayered coating is applied. The coating is tuned to give peak reflectivity for just one wavelength of EUV light (e.g. at about 13.5 nm). Alternatively the lithographic optical element may be a lens as used in for example deep ultraviolet (DUV) lithography. DUV lithography uses longer wavelengths (e.g. about 248 nm, 193 nm, 157 nm, . . . ) compared to EUV lithography (e.g. about 13.5 nm). At these longer wavelengths light may be transmitted by conventional lenses.

Figure 1:
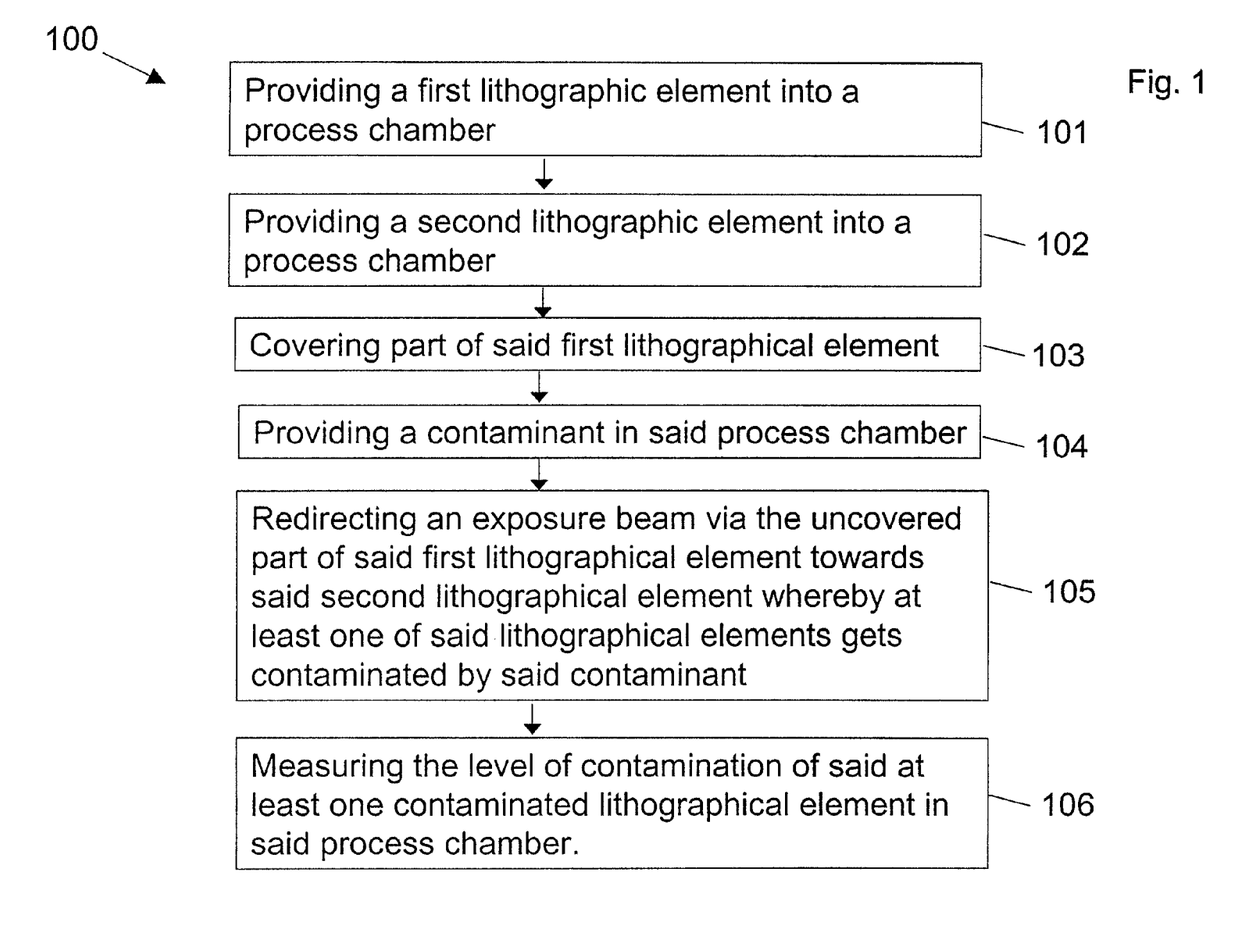
FIG. 1 is a flow chart of a first embodiment of the present invention.

A first embodiment relates to a method for measuring contamination of a lithographic element. Typical processes performed in the method according to the embodiments of the present invention are shown in a flow diagram of an embodiment of a method for measuring contamination (100) in FIG. 1. The method for measuring contamination of a lithographic element comprises providing a first lithographical element in a process chamber (101), providing a second lithographical element in the process chamber (102), covering part of the first lithographical element (103) for providing a reference region on the first lithographic element being the covered part of the element and providing a test region being the uncovered part of the first lithographic element, providing a contaminant in the process chamber (104), directing an exposure beam via the test region of the first lithographical element towards the second lithographical element whereby at least one of the lithographical elements gets contaminated by the contaminant (105), measuring the level of contamination of the at least one contaminated lithographical element in the process chamber (106). The exposure beam also first may be directed on the second lithographical element and thereafter on the first lithographical element, in other words, the sequence in which the lithographical elements are illuminated may differ. The latter is especially the case when contamination is measured in a metrology tool, although it also may be applied in an actual lithographic processing tool.

Figures 2, 2C:
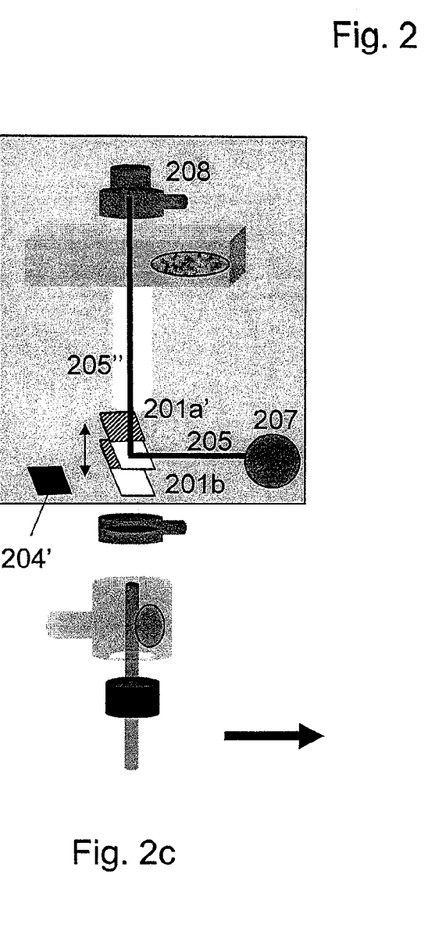
FIGS. 2a to 2d represent the different processes of an embodiment of the present invention for measuring the contamination of a first lithographical element.
Figure 2A:
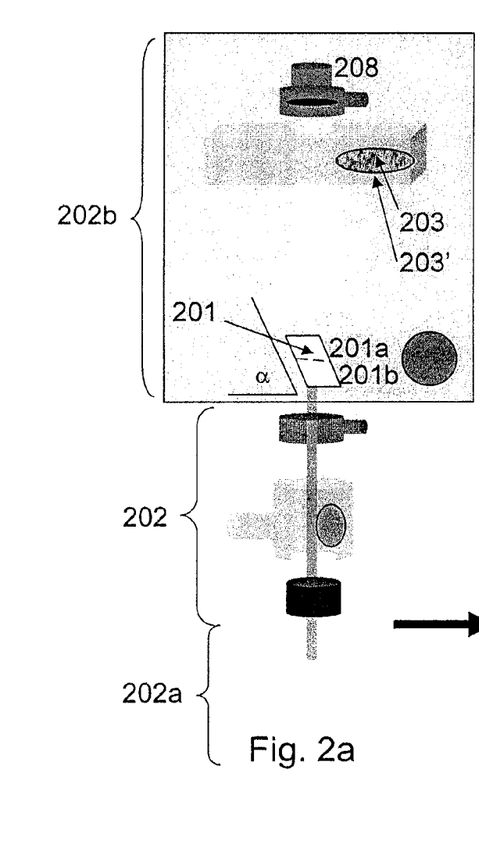
Figure 2B:
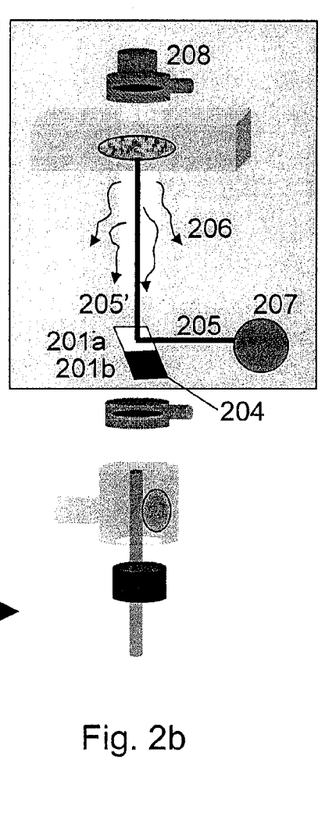

Referring to FIG. 2a, FIG. 2b and FIG. 2c each of these processes will now be described in more detail. In a first process of the method for measuring contamination in a lithographic system a first lithographical element is introduced into a process chamber (101). The process chamber may part of a lithographic metrology system or of a lithographic process system. The providing process also may refer to a situation wherein no active providing is required anymore, e.g. in a system wherein the first lithographical element is already present, such as for example a lithographic system wherein measurement facilities for performing the present method are provided but that is also used for effective lithographic processing. The provision of the first lithographical element therefore may be performed during set-up of the system or in prior actions. In other words, an active providing process may be optional. The first lithographical element (201) may be directly introduced from an atmospheric environment in the lithographic system (not shown in FIG. 2a). However in case of a lithographic system under vacuum, such as for example an EUV lithographic system, the lithographic system needs to be pumped down again to vacuum level after the introduction of the first lithographical element (201). Therefore, for introducing the first lithographical element (201), preferably a load-lock chamber (202) may be used. A load-lock chamber is an atmosphere (202a)-to-vacuum (202b) entry system for facilitating the transfer of objects in and out vacuum systems. For example, in an EUV lithographic system, the environment inside the EUV tool is under vacuum (202b). By using a load-lock chamber (202) the lithographic system can be kept under vacuum when introducing a first lithographical element from an atmospheric environment (202a) into the EUV tool. First the first lithographical element (201) is transferred from the atmospheric environment (202a) in the load-lock chamber (202). Next the load-lock chamber is pumped down to a pressure which is comparable to the pressure in the lithographic system, e.g. about $10^{-7}$ mbar. Next the first lithographical element (201) is transferred from the load-lock chamber (202) into the lithographic system, which is under the same or at least comparable pressure as the load lock (202b). In the lithographic system (202b) the first lithographical element may be positioned on a movable stage such that the first lithographical element is movable into the lithographic system. The first lithographical element may be movable as may be required for the process of comparing the level of contamination as will be explained further.

This first lithographical element may be a lithographical optical element. The first lithographical element may be, e.g., mirror or a lens. In EUV lithography, a reflective mirror is typically used. The reflective mirror may be made with coatings of alternating films of molybdenum (Mo) and silicon (Si). By increasing the number of alternating layers the reflectivity of the mirror can be increased. In DUV lithography, conventional lenses are used. A lens will transmit the electromagnetic radiation, whereas a mirror will reflect the electromagnetic radiation. When using mirror, reflectivity of electromagnetic radiation may be typically measured to characterize the mirror. When using a lens, transmissivity of electromagnetic radiation may be typically measured to characterize the lens. Also contamination of the mirrors or lenses can be measured by measuring their reflectivity or transmissivity respectively.

In a next process of the method for measuring contamination of a lithographic element, a second lithographical element (203) is introduced into the process chamber (102). Again active introduction may be optional as the second lithographic element already may be present in the process chamber, e.g. introduced during installation or during previous actions. For introducing the second lithographical element (203), a load-lock chamber may be used (not shown in FIG. 2a). Alternatively the second lithographical element (203) may also be directly introduced from an atmospheric environment in the lithographic system (as in FIG. 2a). In case of a lithographic system under vacuum, such as for example an EUV lithographic system, the lithographic system needs to be pumped down again to vacuum level after the introduction of the second lithographical element (203).

In another process of the method for measuring contamination of a lithographic element, a part of the first lithographic element is covered (103), providing the reference region (201b). Such covering may be done prior to or after introduction of the contaminant, preferably prior to introduction of the contaminant. The covering certainly needs to be performed prior to exposure of the lithographic elements. With covering part of the first lithographical element (201) is meant that at least a part or reference region (201b) of the first lithographical element (201) is covered and will remain unchanged and can thus serve as a reference when comparing different regions of the first lithographical element. The covered part, referred to as reference region (201b), remains the same before and/or after exposure to the electromagnetic radiation of the exposure beam and/or the contaminant. Neither the contaminant nor the exposure radiation will interact with the covered part or reference region 201b. The uncovered part, referred to as test region (201a), from the first lithographical element will be exposed to the electromagnetic radiation and/or the contaminant. As a consequence the contaminant or exposure radiation will interact with the uncovered part or test region 201a.

The process of covering part of the first lithographical element may comprise shielding the first lithographical element from the contaminant by a shield. Shielding the first lithographical element from the contaminant may comprise providing a hard contact between the shield and the part of the first lithographical element. Alternatively, shielding the first lithographical element from the contaminant may comprise providing a soft contact between the shield and the part of the first lithographical element. Alternatively the shield may be positioned in such a way that the shield avoids radiation to fall onto the reference region, i.e. shadows the reference part of the first lithographical element.

FIG. 2b shows the process of shielding at least part (201b) of the first lithographic element in order to prevent the reference region (201b) to be contaminated. This shielding (204) may be done for example by mechanically using a shutter which moves in front of the reference region (201b) and making a hard contact or soft contact between the shield and the first lithographical element, or which shutter or shield throws a shadow on a region of the first lithographic element, i.e. prevents the radiation incident on the shielded region of the first lithographic element. Dependent on the contaminant the spacing may be different. The spacing preferably is such that no contaminant can reach or interact with the shielded part of the lithographical element. The shield may be positioned in such a way that the contaminant cannot interact with the shadowed part of the lithographical element. The shield may be any material that has the properties to prevent the contaminant from interacting with the underlying part of the lithographical element.

Preferably one reference region is defined on the first lithographical element. Alternatively the reference region may comprise a number of reference zones, e.g. two or three reference zones. Preferably one uncovered part, forming a test region, is defined on the first lithographical element. Alternatively, in another embodiment of the present invention, the uncovered part comprises a plurality of uncovered parts forming a plurality of test zones. More test regions can thus be defined, e.g. two reference zones can be defined, three reference zones can be defined.

Figure 4:
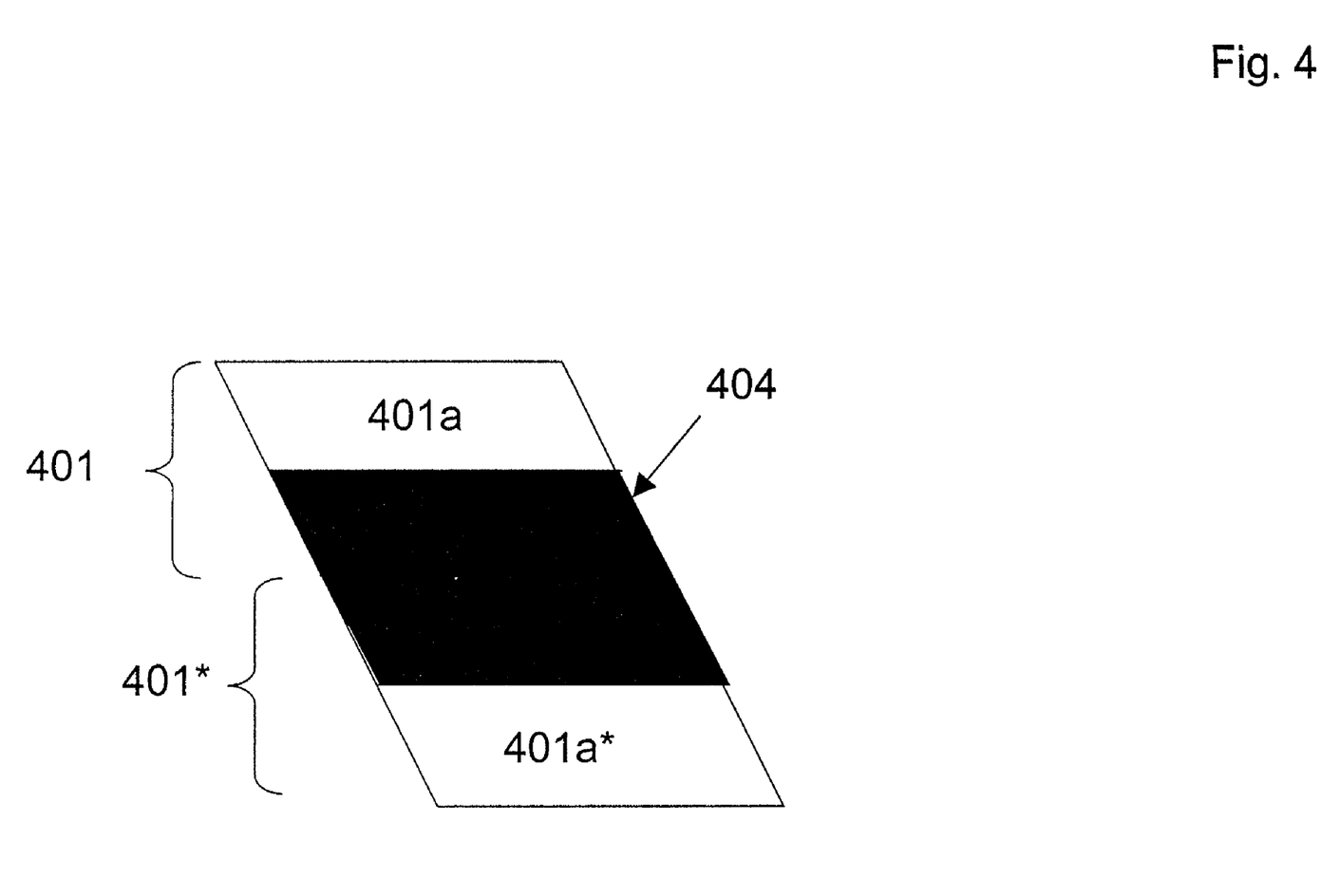
FIG. 4 shows a first lithographical element of one embodiment.

By defining more test zones on the first lithographical element, different properties of the first lithographical element may be analyzed during one measurement. For example—but not limited thereto—if the first lithographical element is a mirror, two reference zones and two test zones can be defined on the mirror (FIG. 4). A mirror can, for example, be fabricated which has a first part (401) containing 40 Mo/Si layers with a specific capping layer on top and a second part (401*) containing 40 Mo/Si layers with no capping layer on top. In the first part (401) one first zone (401b) of the reference region may be covered and a second part (test zone 401a) may remain uncovered. In the second part (401*) of the mirror one first zone (being a second reference zone 401b*) may be covered and a second part (being a second test zone 401a*) may remain uncovered. The reference zones (401*b* and 401*b) may be covered simultaneously by a shield 404**. Alternatively separate shields may be used to cover the reference zones.

In a next process of the method for measuring contamination of a lithographic element, a contaminant is provided into process chamber of the lithographic system (104). The contaminant may be any component which enables contamination of the first and/or second lithographical element. The contaminant may be, for example—but not limited thereto—organic compounds or any gaseous compound. The organic compounds can be directly introduced into the process chamber or can be indirectly introduced into the process chamber. By directly introducing the contaminant is meant introducing the contaminant via an inlet (310)(FIG. 3*a*) into the lithographic system. These are for example gases, such as a carrier gas contaminated with organic compounds mentioned above. By indirectly introducing the contaminant is meant introducing the contaminant by the second lithographical element.

In a particular embodiment of the present invention, the second lithographical element comprises the contaminant.

The second lithographical element may comprise resist. For example, if the second lithographical element (203) is a wafer, this wafer may be covered with a resist (203') comprising the contaminant, which resist is typically used in lithography to define the mask pattern on a wafer. It is known from the prior art that the resist comprises contaminant, since resist outgassing occurs as soon as the wafer (with resist on top) is subjected to vacuum and/or exposed to electromagnetic radiation.

In a next process of the method for measuring contamination of a lithographic element, an exposure beam is directed via the test region of the first lithographical element towards the second lithographical element whereby at least one of the lithographical elements gets contaminated by the contaminant (105).

In an embodiment of the present invention, the first lithographic element gets contaminated by the contaminant in the process of redirecting an exposure beam (205) via the test region of the first lithographical element towards the second lithographical element whereby at least one of the lithographical elements gets contaminated by the contaminant. In this process the first lithographical element is exposed for example by electromagnetic radiation (205) from an EUV source (207) or using any other wavelength which can be used in a lithographic set-up (FIG. 2*b*). Due to the exposure to the beam and the interaction with the contaminant, the non-shielded regions (including the at least one test region (201*a*)) of the first lithographical element (201) will be contaminated. The shielded region or the at least one reference region (201*b*) of the first lithographical element will remain uncontaminated. The first lithographical element may be a mirror (201) and the second lithographical element is a wafer (203) with resist (203') (as contaminant) on top. An EUV source (207) emits EUV electromagnetic radiation (205) onto the mirror (201). Due to the mirror, which is positioned under an angle α, the EUV light (205') is reflected from this mirror (201) to the wafer (203) with resist (203'). As soon as the wafer with resist on top is exposed to the EUV light, resist outgassing will occur (206). The component provided by resist outgassing may contaminate the at least one test region (201*a*) of the mirror, but will not contaminate the at least one reference region (201*b*) of the mirror, due to the shielding from the resist outgassing which is positioned on top of the at least one reference region. Alternatively, DUV light may be used to expose the first lithographical element. In this case the light will not be reflected (as with EUV light), but will be transmitted. The mirror is positioned under an angle α, such that the beam from the beam source is reflected under this angle α from the first lithographical element towards the second lithographical element. This angle α is preferably 45 degrees, but may in principle range from almost zero to almost 90 degrees. The second lithographic element, e.g. wafer, may be scanned during the process of contamination in order to induce enough resist outgassing.

In a subsequent process of the method for measuring contamination of a lithographic element, the contaminant, more particularly the contamination source, may be removed from the process chamber and the process chamber is cleaned. If the contamination rate is sufficiently low compared to the contamination measurement time and/or depending on the accuracy of the measurement required, this process may be not performed. Such a process therefore is optional. With removing the contaminant is meant taking away the contamination source such that further contamination does not further occur. If for example the contaminant is a component of the outgassing of a resist on top of wafer, the wafer with resist on top can be removed, such that it will not be exposed anymore to electromagnetic radiation (FIG. 2*c*) or even removed from the chamber to avoid outgassing under vacuum. If the resist is not exposed anymore to electromagnetic radiation, no resist outgassing will occur. Cleaning of the process chamber may be done, e.g. by outbaking, to eliminate these gases or other contaminants present in the process chamber. Outbaking is the heating of vacuum equipment, particularly workpieces to be included in a vacuum chamber during operation, while maintaining the lowest possible operating pressure, in order to remove adsorbed gas from surfaces and cavities in the vacuum chamber. Also other cleaning methods may be used as known for a person skilled in the art. It will be clear that for obtaining information of the contamination of a lithographic element, such elements will not be cleaned prior to determination of the contamination occurring.

In a next process of the method for measuring contamination of a lithographic element, the level of contamination of the at least one contaminated lithographical element in the process chamber is measured. For this process different preferred embodiments are described. The process preferably comprises uncovering, i.e. remove the cover of the reference region of the first lithographical element. The shielding of the at least one reference region (covered part or reference region) of the first lithographical element is thus removed. With removing the shielding is meant that whatever was protecting, covering or shadowing the at least one reference region is removed (FIG. 2*c*). This "unshielding" may be done for example mechanically using a shutter which moves away (204') from of the at least one reference region (201*b*). After this process, which is done after exposure, the first lithographical element contains at least one part (201*b*) which is unchanged compared to the part before exposure (201*b*) and at least one part (at least one test region) (201*a'*) which is contaminated compared to the part before exposure (201*a*).

In a particular embodiment of the present invention the process of measuring the level of contamination of the at least one lithographical element in the process chamber further is measuring the level of contamination of the first lithographical element (106).

The process of measuring the level of contamination of the first lithographical element in the process chamber further comprises measuring a value for a parameter of the reference region of the first lithographical element, i.e. obtaining a reference value for the parameter, measuring a value for the parameter of the test region of the first lithographical element, i.e. obtaining a test value for the parameter, and determining, e.g. by calculating, the difference between the reference value and the test value. By comparing the level of contamination (which is related to the test value) on the at least on test region with the level of contamination (which is related to the reference value) on the reference region, the difference, e.g. the relative loss of the value of parameter of the first lithographical element due to the contamination by the contaminant may be determined, e.g. calculated.

In case the first lithographic element is a reflective element, e.g. a mirror, depending on the amount of contamination by the contaminant, the reflectivity of the first lithographical element may change. For an EUV lithographic measurement the reflectivity of the mirrors, for example, is preferably around about 70%. Due to contamination, for example due to presence of components resulting from resist outgassing, the reflectivity of the mirrors can deteriorate by a few percentages (typically about 1-2%) depending on the amount of contaminant and exposure dose. As a consequence the lifetime of the optical elements (such as mirror, mask, . . . ) is reduced, which is a major concern in lithography since these optical elements are very expensive. Taking into account that multiple mirrors are used in a EUV lithographic exposure tool, the total loss of reflectivity is increased. It is thus important to keep the change in reflectivity due to contamination as low as possible, preferably smaller than 0.1% or a few 0.1%. To measure the (relative) change of reflectivity of an object due to contamination, the reflectivity from at least one test region of the object is compared with the reflectivity from at least one reference region of the object. Whereas the parameter used for detecting contamination is indicated as being reflectivity, the latter may be adapted to the system and/or lithographic system under test and may for example diffusivity of the surface, specular reflection, total reflection, transmissivity for example in case a lens is used.

Figure 2D:
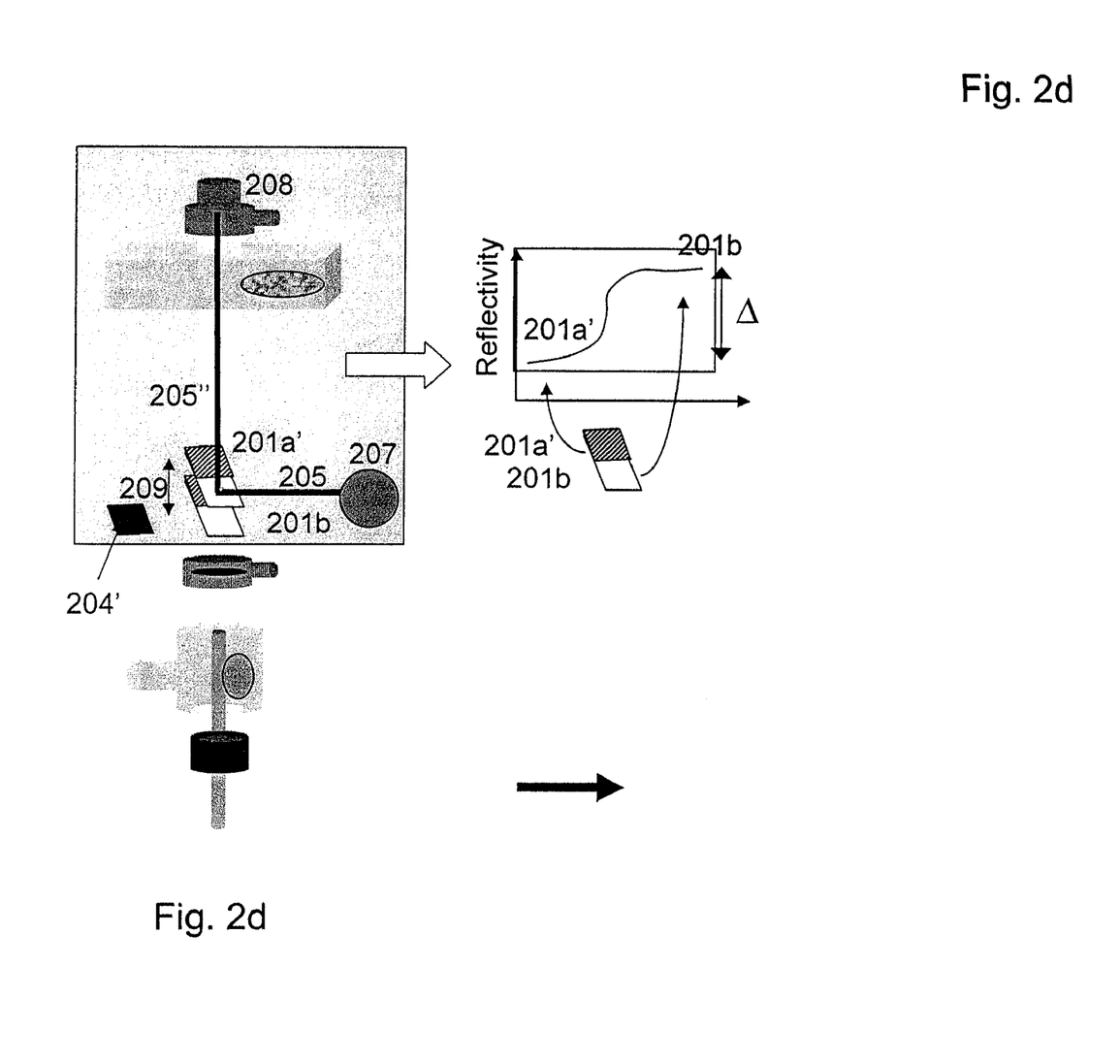

FIG. 2d shows one embodiment of the present invention to measure the contamination of a lithographic optical element in-situ, i.e. in the process chamber. The measurement performed for detecting contamination may be an optical measurement. After removing the shielding from the at least one reference region (201b) of the first lithographical element, the at least one (contaminated) test region (201a') of the first lithographical element is exposed (205) to an exposure beam, e.g. electromagnetic radiation from a radiation source (207). The radiation source thereby may be the same radiation source as used for lithographic processing or for introducing contamination or it may be a separate radiation source used for performing optical measurement of the contamination e.g. by deriving an optical parameter from the contaminated lithographical element. Such a radiation source may provide electromagnetic radiation, e.g. extreme ultraviolet radiation, deep ultraviolet radiation, ultraviolet radiation, visible light, etc. The exposure radiation beam, e.g. light beam will be reflected from the first lithographical element, such that the reflected radiation beam (205") will impinge on a sensor (208) for measuring the reflected radiation intensity of the at least one test region (201a') of the first lithographical element. The contaminant will thus not influence the reflectivity of the first lithographical element; since the contaminant is not exposed anymore (the contaminant was removed). In a following process the movable first lithographical element is moved (209) such that the exposure radiation beam from the source exposes the at least one reference region (201b) of the first lithographical element. Again the radiation is reflected from the at least one reference region towards a sensor which measures the reflected radiation intensity of the at least one reference region of the first lithographical element. FIG. 2d shows a typical reflectivity curve which may be extracted. The difference, Δ, is the difference in reflected radiation intensity between the at least one test region (201a') of the first lithographical element and the at least one reference region (201b) of the first lithographical element. If the at least one test region (201a') is contaminated a decrease will be measured in reflectivity. It should be noted that with this in-situ measurement only relative numbers on the reflectivity can be obtained. For obtaining absolute values on the reflectivity for the at least one test region and the at least one reference region additional reflectivity measurements may be performed ex-situ, i.e. outside the process chamber. These ex-situ reflectivity measurements can be done by any technique well-known for a person skilled in the art such as for example reflectometry. The irradiation source used during the process of contaminating is preferably the same as the irradiation source used for analyzing the lithographical element. Alternatively different irradiation sources may be used.

Alternatively in case DUV radiation is used (instead of EUV radiation), the difference in transmissivity can be measured between the at least one test region and the at least one reference region. After removing the shielding from the at least one reference region of the first lithographical element, the at least one (contaminated) test region of the first lithographical element is analyzed using the radiation of the irradiation source. The irradiation source is preferably the same as the irradiation source used for exposing the first lithographical element, although the invention is not limited thereto. In case DUV radiation is used, the radiation will be transmitted through the first lithographical element, such that the transmitted light beam will impinge on a sensor for measuring the transmissivity of the at least one test region of the first lithographical element. The contaminant will thus not influence the transmissivity of the first lithographical element; since the contaminant is not exposed anymore (the contaminant was removed). In a following process the movable first lithographical element is moved such that the light from the light source exposes the at least one reference region of the first lithographical element. Again the light is transmitted from the at least one reference region towards a sensor which measures the transmissivity of the at least one reference region of the first lithographical element. If an optical parameter of the at least one contaminated lithographic element is to be determined, the latter may be performed using any suitable optical detector, suitable for detecting radiation from the irradiation source used in the contamination measurement. Reflectivity may be measured with a reflectivity sensor, which sensor may be a diode. Alternatively, transmissivity is measured with a transmissivity sensor. This sensor may be a diode. The sensor for measuring the reflectivity may be an EUV sensitive diode, or any other kind of EUV detector, of any complexity. Alternatively, if a electromagnetic radiation source with a wavelength in the DUV region is used, an DUV sensitive diode or any other DUV detector may be used.

In another embodiment of the present invention describing a method for measuring contamination of a lithographic optical element, the second lithographical element is a reticle or a mask. For example, several exposure dose levels can be provided on the reticle (e.g. at different locations) and only one test location is used, e.g. on a mirror (being the first lithographical element).

Figure 3A:
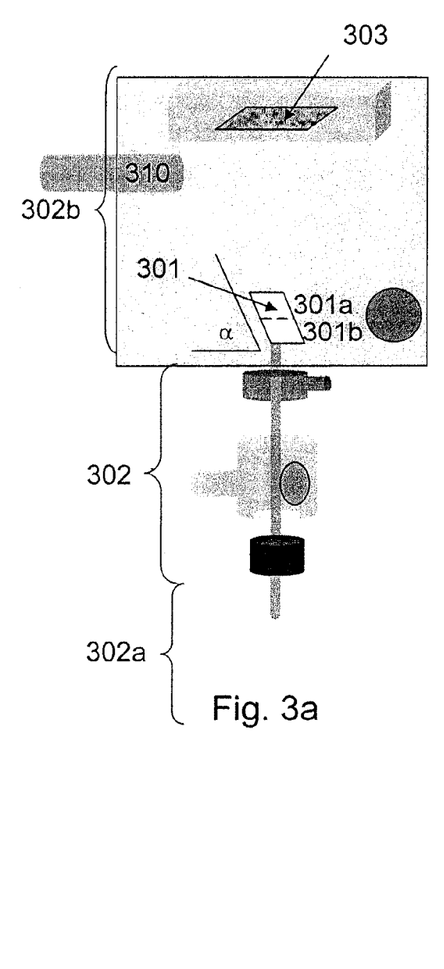
FIGS. 3a to 3c represent the different processes of an embodiment of the present invention for measuring the contamination of a second lithographical element.
Figure 3B:
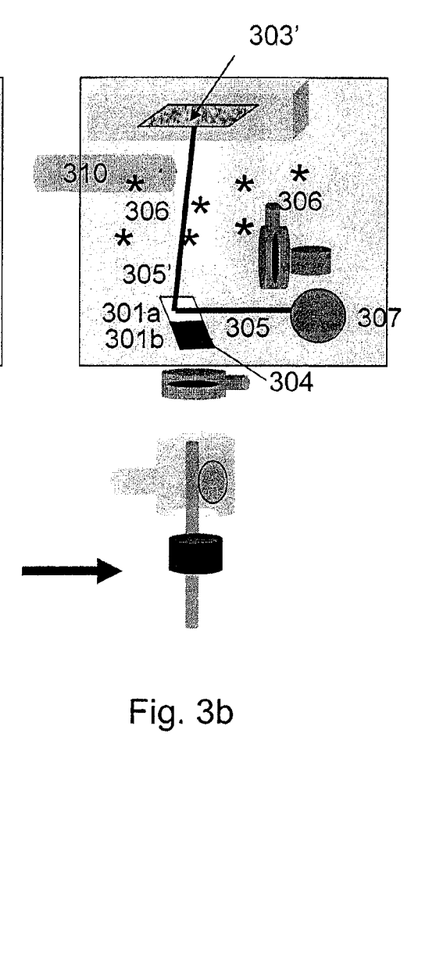
Figure 3C:
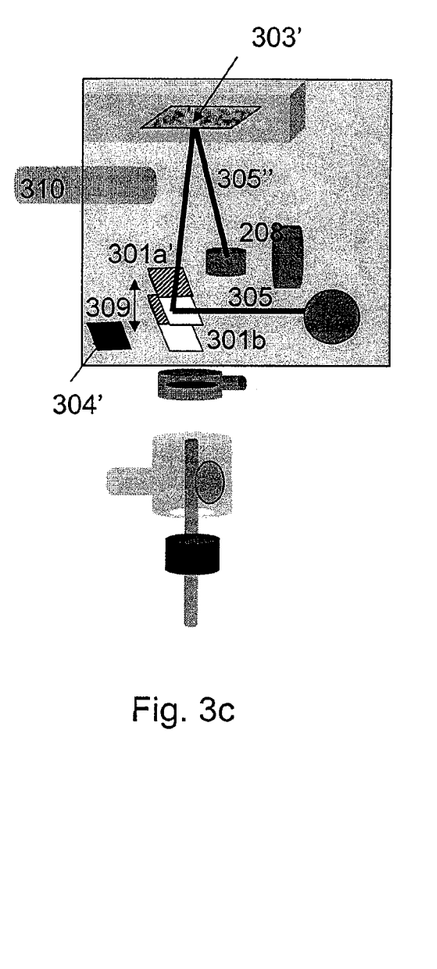

Using FIG. 3a to FIG. 3c each of the processes will now be described in more detail for measuring contamination of a lithographic element wherein the second lithographical element is a mask or a reticle.

In a first process of the method for measuring contamination of the second lithographic element, with the second lithographical element being a mask or a reticle, a first movable lithographic element (301) is introduced in the lithographic system. The first lithographic element (301) may be directly introduced from an atmospheric environment in the lithographic system (not shown in FIG. 3*a*). However in case of a lithographic system under vacuum, such as for example an EUV lithographic system, the lithographic system needs to be pumped again to vacuum level after the introduction of the first lithographical element (301). Therefore, for introducing the first lithographical element (301), preferably a load-lock chamber (302) may be used. The first lithographical element may be positioned on a movable stage such that the first lithographical element is movable in the lithographic system. Similar as above, the first lithographical element may already be positioned in the system, e.g. during installation of the system or during previous actions.

In a next process of the method for measuring contamination of the second lithographic element, a second lithographical element (303), being a reticle or a mask, is introduced into the process chamber. For introducing the second lithographical element (303), a load-lock chamber may be used (not shown in FIG. 3*a*). Alternatively the second lithographical element (303) may also be directly introduced from an atmospheric environment in the lithographic system (as in FIG. 3*a*). Similar as above, the first lithographical element may already be positioned in the system, e.g. during installation of the system or during previous actions.

In a next process of the method for measuring contamination of the second lithographic element, a contaminant is generated in or inserted into the lithographic system. The contaminant (306) may be any component which cause contamination of the first and/or second lithographical element (shown with asterisk in FIG. 3*b*). The contaminant may be, for example but not limited thereto—organic compounds. The organic compounds are directly introduced into the lithographic system. By directly introducing the contaminant (intentional contamination) is meant introducing the contaminant via an inlet (310) (FIG. 3*a*) into the lithographic system. This may be for example gases, such as a carrier gas contaminated with organic compounds as mentioned above.

In another process of the method for measuring contamination of the second lithographic element, with the second lithographical element being a mask or a reticle, at least one reference region is defined by shielding on the first lithographical element and at least one test region is defined on the first lithographical element. With reference region (301*b*) is meant a part or region of the first lithographical element which will remain unchanged during the process and can serve as a reference when measuring the contamination level of the second lithographical element. The reference region (301*b*) thus remains unchanged during exposure to the electromagnetic radiation and/or the contaminant. Shielding or covering should preferably be done before adding the contaminant. The latter allows to substantially reduce or even exclude contamination on the shielded areas, even when the exposure is off. Nevertheless, as the major contamination problems are caused when contamination of the surfaces occurs during exposure of these walls, shielding or covering also could be performed in between introduction of the contaminants and exposing of the optical elements. Thus once the mirror/mask is irradiated, the shielding or covering preferably is present.

Neither the contaminant nor the exposed light will interact with the reference region. With test region (301*a*) is meant a part or region from the first lithographical element which will be exposed to the light and/or the contaminant. The contaminant or exposed light will interact with the test region. Preferably one reference region is defined on the first lithographical element. Alternatively the reference region may comprise more than one reference zone, e.g. two or three reference zones. Preferably one test region is defined on the first lithographical element. Alternatively the test region may comprise more than one test zone, e.g. two or three reference zones.

The at least one reference region of the first lithographical element is shielded (FIG. 3*b*), in order to prevent the at least one reference region (301*b*) to be contaminated. With shielded is meant that the reference region (301*b*) is covered (304) such that it will not be contaminated when being subject to the contaminant, or at least is covered such that it will not be subject to the contaminant and exposure at the same time. This shielding (304) may be done for example mechanically using a shutter which moves in front of the reference region (301*b*) thereby shadowing the reference region on the first lithographic element. Another possibility to shield the at least one reference region of the first lithographical element may be any method that causes a soft contact or hard contact in between the shield and the at least one reference region of the first lithographical element. Any shielding may be used, e.g. one causing a shadow or a method providing soft contact or hard contact between a shield and the first lithographic element, e.g. a mirror.

In a next process of the method for measuring contamination of the second lithographic element, with the second lithographical element being a reticle or a mask, an exposure beam (305, 305') is directed via the test region of the first lithographical element towards the mask or reticle whereby at least one of the lithographical elements gets contaminated by the contaminant. Due to the inserted contaminants (306) the second lithographic element, being a mask or a reticle, will be contaminated (303'). Possibly also the test region of the first lithographic element, e.g. a mirror (301*a'*), may be contaminated. Due to the exposure to radiation (305, 305') and the interaction with the contaminant, e.g. from other parts of the tool, the non-shielded zones (the at least one test region (301*a*)) of the first lithographical element (301) and the second lithographic element (303') will be contaminated.

The shielded region or the at least one reference region (301*b*) of the first lithographical element will remain substantially uncontaminated. For example, the first lithographical element is a mirror (301) and the second lithographical element is a mask or reticle (303). An EUV source (307) emits EUV light (305) onto the mirror (301). Due to the mirror which is positioned under an angle $\alpha$, such as 45° plus or minus 6°, the EUV light (305') is reflected from this mirror (301) to the mask or reticle (303). The contaminant (306) present in the vacuum chamber may contaminate the at least one test region (301*a*) of the mirror, but will not contaminate the at least one reference region (301*b*) of the mirror, due to the shielding which is positioned on top of the at least one reference region. Also the reticle or mask will be contaminated by the contaminant (306), since a mask in EUV comprises a mirror.

The second lithographic element, e.g. the mask or reticle, will be typically scanned during the process of contamination. Different test zones may be defined on the second lithographic element to compare the level of contamination between the test regions of the second lithographic element.

In a next process of the method for measuring contamination of the second lithographic element, with the second lithographical element being a reticle or a mask, the contaminant is removed from the chamber. If the contamination rate is sufficiently low compared to the contamination measurement time and/or depending on the accuracy of the measurement required, this process may be not performed. Such a process therefore is optional. With removing the contaminant is meant taking away the contaminant such that it cannot further contaminate. If for example the contaminant (306) is a gas which is present in the vacuum chamber, the method furthermore may comprise removing the contamination present on the system walls e.g. by a cleaning process of the vacuum chamber, e.g. outbaking, can be performed to eliminate these gases. In other words, the method may comprise an additional process of cleaning the chamber.

In a next process of the method for measuring contamination of the second lithographic element, the second lithographical element being a reticle or a mask, the shielding of the at least one reference region of the first lithographical element is removed. With removing the shielding is meant that whatever was covering the at least one reference region is removed (FIG. 3c). This "unshielding" may be done for example mechanically using a shutter which moves away (304') from of the at least one reference region (301b). After this process, which is done after exposure, the first lithographical element contains at least one reference region (301b) which is remained unchanged and at least one test region (301a') which is contaminated. The second lithographical element, being a mask or reticle (303'), is also contaminated.

In a next process of the method for measuring contamination of the second lithographic element, the second lithographical element being a reticle or a mask, the contamination level of the second lithographical element is measured in-situ, i.e. in the process chamber. This measurement is done by redirecting the exposure beam (305) via the reference region of the first lithographical element towards the second lithographical element, and further towards a sensor (308). The reference part is now no longer shielded or covered. During this process a test value for a parameter is measured, which is preferably the reflectivity of the contaminated reticle. For wavelengths where transmissive masks are used, transmissivity of the contaminated reticle or mask may be measured in a similar way. In this case lenses are used instead of mirrors for transmitting the electromagnetic radiation from the beam source via the first lithographical element towards the second lithographical element towards the sensor. In one embodiment, the contamination of the second lithographical element is measured or determined by measuring an optical parameter such as transmissivity or reflectivity on a reference zone on the second lithographical element and a test zone on that second lithographical element. The reference zone on the second lithographical element may be obtained by shielding the second lithographical element, similar as described above, or may be obtained from a zone on the second lithographical element not being exposed with an exposure beam. In the latter case, a small amount of contamination may be present in the reference zone, although large contamination only takes place in exposed regions.

Alternatively the first lithographical element may be moved (309) during the process of directing the exposure beam (305) via the uncovered reference region, i.e. previously covered part, of the first lithographical element towards the second lithographical element towards a sensor (308). Additionally to the reflectivity or transmissivity of the reticle (mask), also the reflectivity or transmissivity of the contaminated part of the first lithographical element, e.g. mirror, can be taken into account. It is known that the capping layer of a reticle may be different from the capping layer of mirror. This means a reticle may be contaminated in another way or to another degree than a mirror when being exposed to a contaminant, due to the different material properties of the reticle and the mirror. By combining the measurement of the contamination of the reticle, e.g. reflectivity of the reticle, with the measurement of the contamination of the mirror, e.g. reflectivity of the mirror, a comparison and characterization can be made on the contamination behavior on reticle and/or on mirror. It is an advantage of one embodiment that such a characterization can be done in-situ and simultaneously by one measurement.

For example, in a EUV lithographic measurement the reflectivity of the mirrors, for example, is preferably around 70%. Due to the intentional contamination, the reflectivity of the mirrors can deteriorate by a few percents typically 1-2%, or maybe even more. As a consequence the lifetime of the optical elements (such as mirror, mask, . . . ) is reduced, which is a major concern in lithography since these optical elements are very expensive. It is thus important to keep the change in reflectivity due to contamination as low as possible. As a plurality of mirrors is present in an EUV lithographic system, additionally the contamination of the mirrors can be taken into account, when measuring the contamination of the reticle. If only the reticle would contaminate and not the mirrors the impact on throughput would be negligible (about 1-2%). To measure the (relative) change of reflectivity of the first and the second lithographic element due to contamination, the reflectivity from at least one test region of the first lithographic element is compared with the reflectivity from at least one reference region of the lithographic element. Furthermore these reflectivities are compared with the reflectivity of the second lithographical element, begin a mask or a reticle. After removing the shielding from the at least one reference region (301b) of the first lithographical element, the at least one (contaminated) test region (301a') of the first lithographical element is exposed again by the exposure beam (305). The beam will be reflected from the first lithographical element, such that the reflected radiation beam will impinge on the second lithographical element (303'). The reflected light beam will be reflected from the second lithographical element towards a sensor for measuring the test reflectivity being a combination of the reflectivity of the at least one test region (301a') of the first lithographical element and the reflectivity of the second lithographical element (303') (FIG. 3c). The contaminant will thus not influence the reflectivity of the first lithographical element or the second lithographical element, since the contaminant is not exposed anymore (the contaminant was removed). In a following process the movable first lithographical element is moved (309) such that the light from the light source exposes the at least one reference region (301b) of the first lithographical element. Again the light is reflected from the at least one reference region towards the second lithographical element, reflecting the light beam further towards a sensor which measures the reference reflectivity, being a combination of the reflectivity of the at least one reference region of the first lithographical element and the reflectivity of the second lithographical element. The difference, Δ, is the difference between the test reflectivity and the reference reflectivity. If the at least one test region (301a') is contaminated a decrease will be measured in reflectivity. If the second lithographical element is contaminated a decrease will be measured in reflectivity. It should be noted that with this in-situ measurement only relative numbers on the reflectivity can be obtained. For obtaining absolute values on the reflectivity for the at least one test region and the at least one reference region additional reflectivity measurements may be performed ex-situ. Alternatively in case DUV light is used (instead of EUV light), the difference in transmissivity can be measured in between the at least one test region and the at least one reference region.

Figure 5:
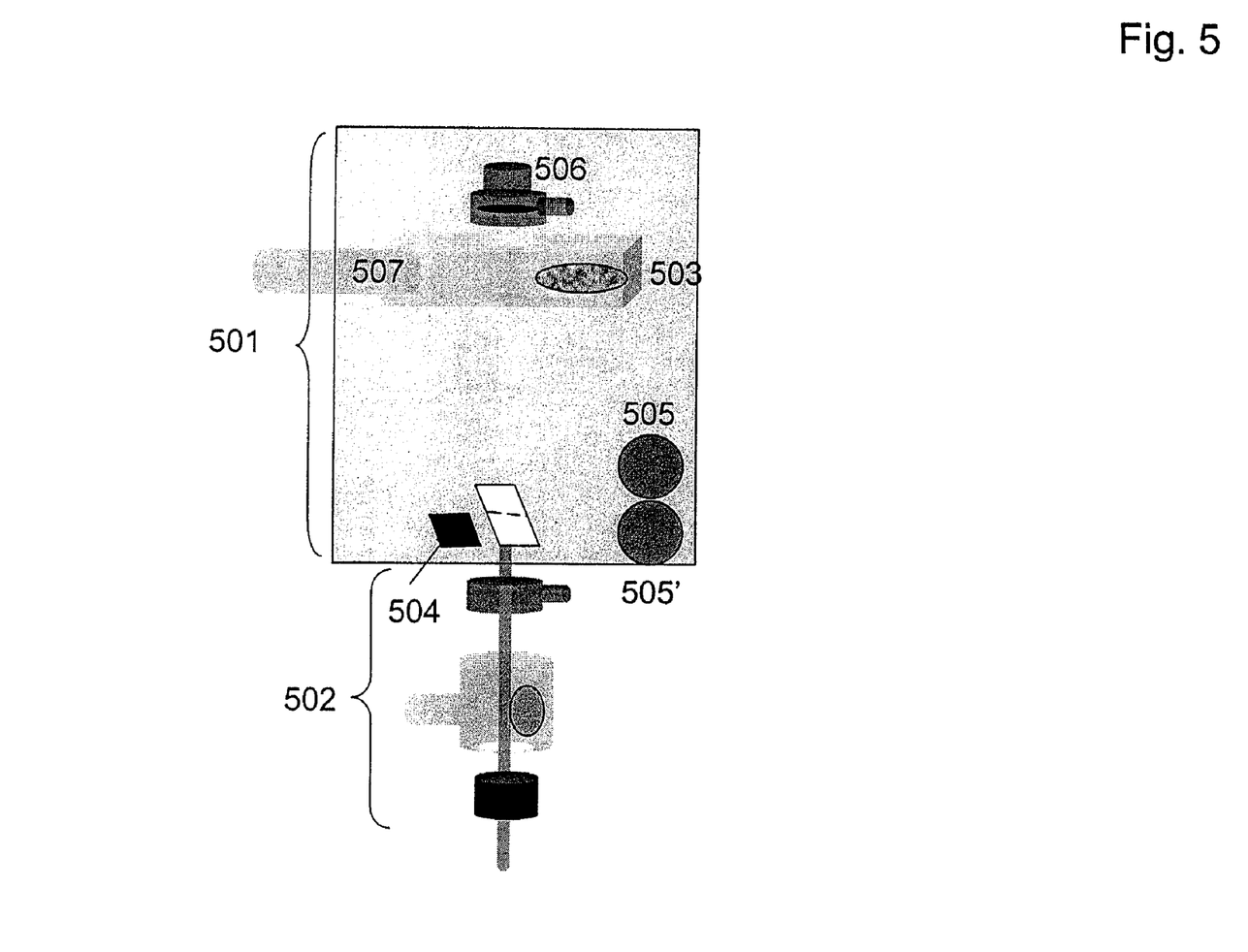
FIG. 5 shows a system for measuring the contamination of a lithographic element of an embodiment of the present invention.

According to one embodiment, a system for measuring contamination of a lithographic element is provided. The system comprises a process chamber (501) (see FIG. 5). It may comprise an element (502) for introducing a first lithographic element into the process chamber and an element for introducing a second lithographic element (503) into the process chamber. The system also comprises an energy source in the process chamber for irradiating a first and second lithographic element introduced in the system. The latter furthermore may induce contaminating at least one of the lithographic elements by directly or indirectly exposing the at least one of the lithographic elements to radiation from this energy source (505). Alternatively, the process chamber may furthermore comprise an inlet for providing contamination to the process chamber. The system further comprises an element for covering at least part of the first lithographic element such that the covered part of the first lithographic element is not contaminated when exposed by the first energy source (505), thereby providing a reference region on the first lithographic element. The system further comprises a sensor (506) for measuring contamination and an inlet for introducing a contaminant (507). In this way, the system is adapted for measuring a parameter of the at least one of the lithographic elements. Preferably the process chamber is under vacuum e.g. when using an EUV energy source (505). Additionally the system may comprise a second energy source (505'). In this case a first energy source (505), e.g. a high power energy source, e.g. EUV source, may be used for directly or indirectly exposing the at least one of the lithographic elements so that contamination of at least one of the lithographic elements occurs. A second energy source (505'), e.g. a low power energy source, may be used for measuring a parameter of the at least one of the lithographic elements, e.g. reflectivity. In preferred embodiments, contamination is studied on areas of the lithographic element that are exposed, as contamination typically will be strong in such areas. The sensor may be a reflectivity sensor or a transmissivity sensor depending on the energy source used. The sensor may comprise a diode. The system for measuring contamination of lithographical element may possibly also be integrated into a lithograph process tool, i.e. a lithographic exposure tool.

It is to be understood that although preferred embodiments, specific constructions and configurations, as well as materials, have been discussed herein for devices according to the present invention, various changes or modifications in form and detail may be made without departing from the scope and spirit of this invention. For example, any formulas given above are merely representative of procedures that may be used. Functionality may be added or deleted from the block diagrams and operations may be interchanged among functional blocks. Steps may be added or deleted to methods described within the scope of the present invention.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A method of measuring contamination of a lithographical element comprising:
   providing a process chamber with a first lithographical element, a second lithographical element, and a contaminant therein;
   covering part of the first lithographical element, thus providing a reference region on the first lithographical element being the covered part of the first lithographical element and a test region on the first lithographical element being the uncovered part of the first lithographical element;
   directing an exposure beam via the test region of the first lithographical element towards the second lithographical element such that at least one of the lithographical elements gets contaminated by the contaminant;
   uncovering the covered part of the first lithographical element, thus providing an uncovered reference region; and
   optically measuring the level of contamination of the at least one contaminated lithographical element in the process chamber.

2. The method according to claim 1, wherein the covering of part of the first lithographical element comprises, either providing a shield in direct contact with the first lithographical element to cover at least part of the first lithographical element, or providing a shield for shadowing at least part of the first lithographical element.

3. The method according to claim 1, wherein the optically measuring of the contamination level comprises measuring an optical parameter on the test region and the reference region.

4. The method according to claim 1, wherein the first lithographical element is a lithographical optical element.

5. The method according to claim 1, further comprising removing the contaminant from the process chamber before measuring the level of contamination of the at least one contaminated lithographical element in the process chamber.

6. The method according to claim 1, wherein the optically measuring of the contamination level comprises measuring an optical parameter on the test region and the uncovered reference region.

7. The method according to claim 1, wherein the measuring of the level of contamination of the first lithographical element in the process chamber comprises:
   measuring a value for a parameter at the uncovered reference region of the first lithographical element, the measured value being the reference value of the parameter,
   measuring a value for the parameter at the test region of the first lithographical element, the measure value being the test value of the parameter,
   determining the difference between the reference value and the test value.

8. The method according to claim 7, wherein the measuring of the reference value of the parameter comprises redirecting the exposure beam via the reference region of the first lithographical element towards a sensor.

9. The method according to claim 7, wherein the measuring of the test value of the parameter comprises redirecting an exposure beam via the test region of the first lithographical element towards a sensor.

10. The method according to claim 1, wherein the second lithographical element is a mask.

11. The method according to claim 1, wherein the second lithographical element comprises the contaminant.

12. The method according to claim 11, wherein the second lithographical element comprises resist, the resist comprising the contaminant, the contaminant being provided in the process chamber by outgassing of the resist.

13. The method according to claim 1, wherein the optically measuring of the level of contamination of the at least one contaminated lithographical element in the process chamber comprises measuring the level of contamination of the second lithographical element in the process chamber.

14. The method according to claim 13, wherein the optically measuring of the level of contamination of the second lithographical element further comprises:

measuring a second element test value for the parameter at the test region of the second lithographical element by redirecting the exposure beam via the reference region of the first lithographical element towards the second lithographical element and further towards a sensor.

15. The method according to claim 14, wherein the measuring of the second element test value further comprises redirecting the exposure beam via the test region of the first lithographical element towards the second lithographical element and further towards a sensor.

16. The method according to claim 1, wherein the first lithographical element is a mirror or a lens.

17. The method according to claim 16, wherein the parameter is the reflectivity of the mirror or the transmissivity of the lens.

18. The method according to claim 17, wherein the sensor is either a reflectivity sensor or a transmissivity sensor, for the mirror or the lens, respectively.

19. The method according to claim 1, wherein the test region comprises a plurality of test zones.

20. The method according to claim 1, wherein the reference region comprises a plurality of reference zones.

21. A system for measuring contamination of a lithographical element comprising
a process chamber;
a first lithographical element and a second lithographical element;
a contamination source for providing a contaminant,
a first energy source for providing a first energy beam in the process chamber, the energy beam at least adapted to cause contamination of at least one of the first and second lithographical elements by directly or indirectly exposing the at least one of the first and second lithographical elements in the presence of the contaminant;
a sensor for measuring contamination; and
a cover element configured to cover at least part of the first lithographical element such that the covered part of the first lithographical element is not contaminated when the first lithographical element is exposed by the first energy beam.

22. The system according to claim 21, wherein the first energy source emits electromagnetic radiation in the extreme ultra-violet range.

23. The system according claim 22, wherein the sensor is an optical sensor.

24. A system for measuring contamination of a lithographical element comprising:

means for accommodating a first lithographical element, a second lithographical element, and a contaminant;

means for covering part of the first lithographical element, thus providing a reference region on the first lithographical element being the covered part of the first lithographical element and a test region on the first lithographical element being the uncovered part of the first lithographical element;

means for directing an exposure beam via the test region of the first lithographical element towards the second lithographical element such that at least one of the lithographical elements gets contaminated by the contaminant;

means for uncovering the covered part of the first lithographical element, thus providing an uncovered reference region; and means for optically measuring the level of contamination of the at least one contaminated lithographical element in the process chamber.

* * * * *